(12) United States Patent
Saalsaa

(10) Patent No.: US 7,106,835 B2
(45) Date of Patent: Sep. 12, 2006

(54) METHOD AND SYSTEM FOR INTEGRATING A COMPUTER AIDED DISPATCH SYSTEM WITH AN EMERGENCY MEDICAL DISPATCH PROTOCOL

(75) Inventor: Richard Saalsaa, Salt Lake City, UT (US)

(73) Assignee: Medical Priority Consultants, Inc., Salt Lake City, UT (US)

( * ) Notice: Subject to any disclaimer, the term of this patent is extended or adjusted under 35 U.S.C. 154(b) by 0 days.

(21) Appl. No.: 10/124,786

(22) Filed: Apr. 16, 2002

(65) Prior Publication Data

US 2003/0195394 A1 Oct. 16, 2003

(51) Int. Cl.
*H04M 11/04* (2006.01)
(52) U.S. Cl. .............................. 379/45; 379/49; 379/37
(58) Field of Classification Search .................. 379/45, 379/37, 49; 340/505, 539.1, 539.13, 540, 340/5.61, 825.49, 573.1; 455/404.2, 457, 455/11.1; 700/108; 705/2, 7, 11
See application file for complete search history.

(56) References Cited

U.S. PATENT DOCUMENTS

| | | | | |
|---|---|---|---|---|
| 4,926,495 A | * | 5/1990 | Comroe et al. ............. | 455/508 |
| 5,805,670 A | * | 9/1998 | Pons et al. ..................... | 379/45 |
| 5,857,966 A | * | 1/1999 | Clawson ..................... | 600/300 |
| 5,989,187 A | | 11/1999 | Clawson ..................... | 600/300 |
| 6,004,266 A | | 12/1999 | Clawson ..................... | 600/300 |
| 6,010,451 A | | 1/2000 | Clawson ..................... | 600/300 |
| 6,053,864 A | | 4/2000 | Clawson ..................... | 600/300 |
| 6,076,065 A | | 6/2000 | Clawson ........................ | 705/2 |
| 6,078,894 A | * | 6/2000 | Clawson et al. ............. | 705/11 |
| 6,106,459 A | | 8/2000 | Clawson ..................... | 600/300 |
| 2003/0028536 A1 | * | 2/2003 | Singh et al. .................. | 707/10 |

* cited by examiner

*Primary Examiner*—Melur Ramakrishnaiah
(74) *Attorney, Agent, or Firm*—John R. Thompson; Stoel Rives LLP

(57) ABSTRACT

An interface between a computer aided dispatch system and an emergency medical dispatch protocol is provided. Able to operate in either a resident or a non-resident mode, this invention coordinates the transfer of control and information between the computer aided dispatch system and the emergency medical dispatch protocol to improve the efficiency of emergency medical response resources while maintaining the certainty of the use of an established medical response and instruction protocol.

14 Claims, 10 Drawing Sheets

METHOD AND SYSTEM FOR INTEGRATING A COMPUTER AIDED DISPATCH SYSTEM WITH AN EMERGENCY MEDICAL DISPATCH PROTOCOL

BACKGROUND OF INVENTION

1. Field of the Invention

This invention relates to methods and systems for integrating computer applications. More specifically, this invention relates to methods and systems for integrating a computer aided dispatch (CAD) system with a medical protocol interrogation process operating on a computer system.

2. Description of Related Art

A variety of computer software interface methods and systems have been proposed to provide an interface between two or more previously disconnected computer program methods. Generally, these prior systems and methods are not adapted to function with a computer aided dispatch system and a medical protocol interrogation process.

The reader is referred to the following U.S. patent documents for general background material. Each of these patents is hereby incorporated by reference in its entirety for the material contained therein.

U.S. Pat. No. 5,857,966 describes a method and system for receiving processing and responding to emergency medical calls for patients who have fainted or are unconscious.

U.S. Pat. No. 5,989,187 describes a method and system for providing emergency medical counseling to childbirth patients remotely.

U.S. Pat. No. 6,004,266 describes a method and system for receiving, processing and responding to emergency medical calls for patients with heart problems.

U.S. Pat. No. 6,010,451 describes a method and system for providing emergency medical counseling to choking patients remotely.

U.S. Pat. No. 6,053,864 describes a method and system for providing emergency medical counseling to arrest patients remotely.

SUMMARY OF INVENTION

It is desirable to provide a method and system for combining a computer aided dispatch system with an emergency medical dispatch protocol that provides an integrated dispatch system which enables a call taker to rapidly and safely navigate through the medical protocol, wherein key questions and answers are pre-determined in the logic of an expert system to calculate an appropriate determinate level and thereby the appropriate emergency medical response. The determinate level provides a categorization code of the type and level of the incident, the code is provided to a Computer Aided Dispatch system, which is a tool used by dispatchers to track and allocate emergency response resources, for processing.

Accordingly, it is an object of this invention to provide an interface between a computer aided dispatch system and an emergency medical dispatch protocol.

Another object of this invention is to provide an interface between a computer aided dispatch system and an emergency medical dispatch protocol, which enhances the cooperation between the two processes.

A further object of this invention is to provide an interface between a computer aided dispatch system and an emergency medical dispatch protocol, which operates in a multi-tasking environment.

A still further object of this invention is to provide an interface between a computer aided dispatch system and an emergency medical dispatch protocol, which enables a call-taker to rapidly, and consistently navigate through a medical protocol.

It is another object of this invention to provide an interface between a computer aided dispatch system and an emergency medical dispatch protocol in which key questions and answers are pre-determined in internal logic to generate an appropriate response determinate.

It is a further object of this invention to provide an interface between a computer aided dispatch system and an emergency medical dispatch protocol, which provides quality assurance procedures.

Another object of this invention is to provide an interface between a computer aided dispatch system and an emergency medical dispatch protocol that includes a reporting capability to measure the performance of individual staff and overall center performance.

A further object of this invention is to provide an interface between a computer aided dispatch system and an emergency medical dispatch protocol that provides a standardized coding system for use in the computer aided dispatch system.

A still further object of this invention is to provide an interface between a computer aided dispatch system and an emergency medical dispatch protocol that communicates the type and level of criticality of the incident from the protocol to the computer aided dispatch system.

A further object of this invention is to provide an interface between a computer aided dispatch system and an emergency medical dispatch protocol that, in combination with a computer aided dispatch system and the protocol, provides the means of tracking and allocating emergency medical resources.

Additional objects, advantages and other novel features of this invention will be set forth in part in the description that follows and in part will become apparent to those skilled in the art upon examination of the following or may be learned with the practice of the invention. The objects and advantages of this invention may be realized and attained by means of the instrumentalities and combinations particularly pointed out in the appended claims. Still other objects of the present invention will become readily apparent to those skilled in the art from the following description wherein there is shown and described the preferred embodiment of this invention, simply by way of illustration of one of the modes best suited to carry out this invention. As it will be realized, this invention is capable of other different embodiments, and its several details and specific steps are capable of modification in various aspects without departing from the concept of this invention. Accordingly, the objects, drawings and descriptions should be regarded as illustrative in nature and not as restrictive.

BRIEF DESCRIPTION OF DRAWINGS

The accompanying drawings incorporated in and forming a part of the specification, illustrate a preferred embodiment of the present invention. Some, although not all, alternative embodiments are described in the following description. In the drawings.

Figure 1:
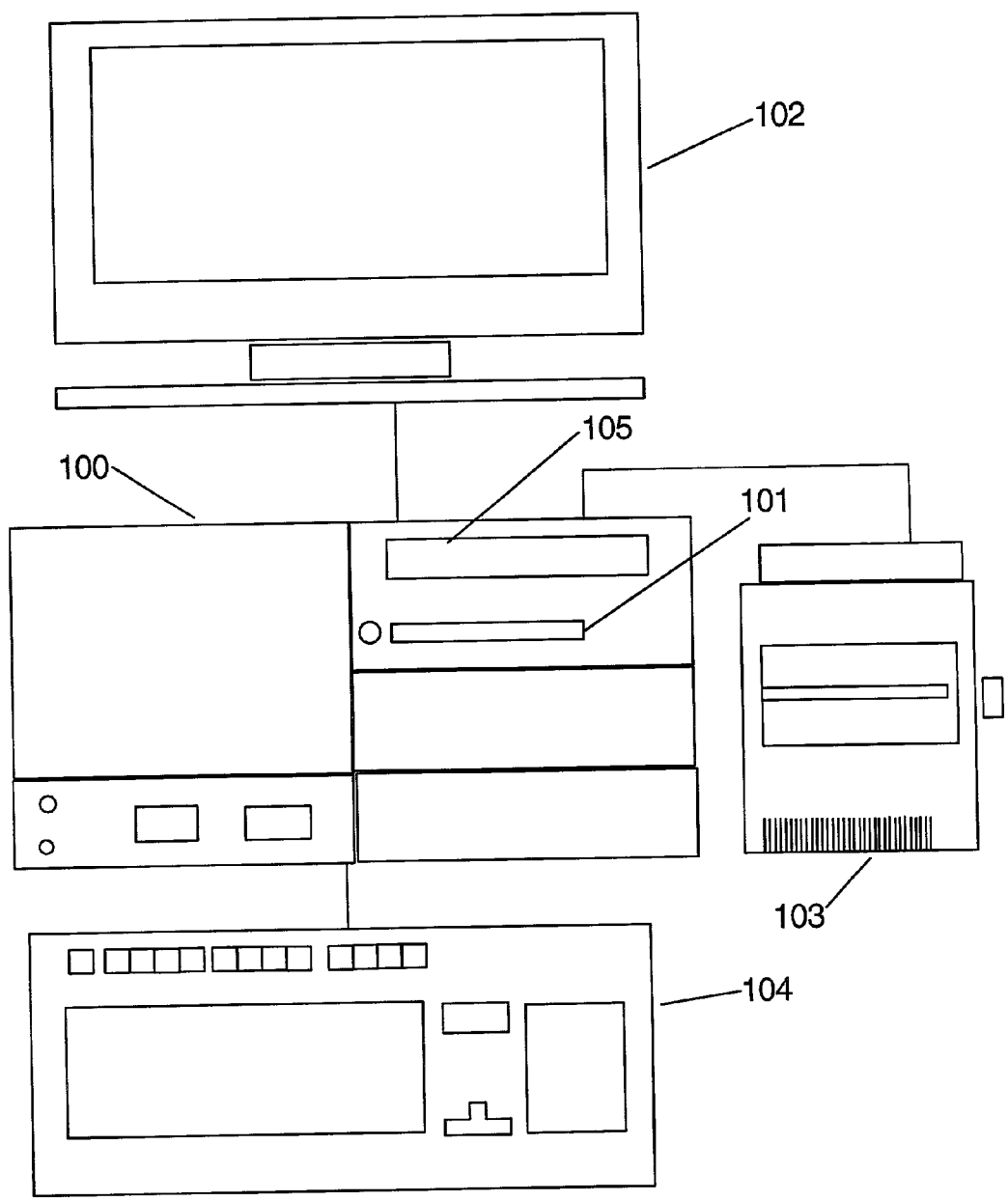
FIG. 1 is a top-level system block diagram showing the preferred computer hardware employed in this invention.

Reference will now be made in detail to the present preferred embodiment of the invention, an example of which is illustrated in the accompanying drawings.

DETAILED DESCRIPTION

This invention is a method and system for combining and facilitating the operation of a computer-aided dispatch (CAD) system with an emergency medical dispatch system which enables an emergency call taker to rapidly, safely and consistently navigate through an emergency medical protocol.

CAD is a tool used by dispatchers to track and allocate resources. The primary information used in this task is location information of both the incident and units, unit availability and the type of incident. CAD systems typically use third party solutions, such as E-911, vehicle location transponders and MDT's for automating the location and availability tasks.

In its present preferred embodiment, this invention works with a software expert system, wherein key questions and answers are processed according to predetermined logic to both provide the correct emergency medical dispatch response and the appropriate doctor-approved post-dispatch instructions to the call taker before professional help arrives. The reader should note that for the purposes of this disclosure, the following terms shall be treated as synonyms, in the present preferred embodiment of the invention: expert system, software expert system, medical dispatch system or program, emergency medical dispatch expert system, ProQA and derivations thereof. The software expert system calculates a determinate value from the caller's responses and uses this determinate value to present the appropriate response for use by the dispatcher. Since many calls for medical service are not true medical emergencies, it is important to prioritize the calls in several ways. First, calls that are true emergencies should be dispatched first. Second, if an agency has units with different capabilities, the more severe medical problems should receive the more advanced units. And finally, if lights-and-siren are not needed from a medical standpoint, they should not be used, thereby increasing the safety of all those on the road.

The present expert system provides a protocol, which includes a consistent carefully chosen set of questions, the responses to which are used to calculate a determinate value. The determinate value is used to classify the degree of emergency and to recommend the appropriate level of emergency medical response, both in terms of the type of equipment and the required speed of response. Since the questions asked and the recommendations that are made by the expert system deal directly with life and death decisions, the protocols used with this invention shall have passed through a rigorous medical review by a panel of doctors and EMS public safety experts who specialize in emergency medicine.

While many medical calls are not true emergencies, all situations can benefit from medical evaluation and instruction. Prior to the arrival of professional help on-scene, the expert system provides instructions that are appropriate to the type of call, from minor lacerations to someone who is not breathing.

The preferred expert system used with this invention has a built-in reporting capability to statistically measure the performance of individual staff and overall center performance. These statistics include compliance rates; call processing statistics and peer measurements. The expert system also determines the incident code, via a standardized coding system from an established protocol.

The expert system, in the preferred embodiment, can be run as a stand-alone application. However, because the information the expert system provides can be very effectively used as a tool within the CAD environment when properly integrated, this invention provides this integration.

The use of this invention begins with the creation of a medical call incident. A CAD call taker identifies the call as requiring access to the expert system, which is then called into operation to begin the Emergency Medical Dispatch (EMD) interrogation. Once the type and level of incident has been determined, the program returns to the CAD for processing of the information. In a horizontal dispatch center, the call taker then continues the expert system process while a radio dispatcher allocates the necessary equipment and performs the dispatch (and can obtain a summary of information from the expert system about the incident). In a vertical dispatch center, the call taker/dispatcher takes the required time to allocate and dispatch the emergency dispatch units, returning to the expert system for further instructions. The expert system has the capability to sense a change of dispatch, through the reconfiguration process (generally brought about by changing the answers to key questions during subsequent interrogation of the caller). Alerts and new incident codes are also communicated to CAD for any necessary processing. The preferred expert system is capable of handling multiple incidents, through the ability to place the call "on hold" and return a later time. Finally, once the call taker has completed the call, the expert system can be used to recall a closed incident if the caller accesses the center again.

FIG. 1 shows a top-level system block diagram showing the preferred computer hardware employed in this invention. In its present preferred embodiment, the process of this invention interfacing between a CAD program process and an expert emergency medical dispatch system is performed on a digital computer system 100. In its present embodiment the digital computer system or workstation 100 includes a processor 105 performing the required computations; a memory unit 101 in electronic communication with the processor 105 for storing the computer 100 operating system, application programs including the CAD program, the expert medical dispatch program, and the interface program, and data storage; a display unit 102 in electronic communication with the processor 105 for viewing the displayed instructions and inquiries; an user input device 104 in electronic communication with the processor 105 for providing the mechanism of inputting response data; and a hardcopy printer 103 in electronic communication with the processor 105 for providing reports. Present embodiments of the invention, run under the following operating systems MS-DOS, Windows, Unix, AIX, CLIX, QNX, OS/2, and Apple. Alternatively, it is expected that future embodiments will be adapted to execute on other future operating systems.

In the present embodiment of the invention four files are used for configuration and communication purposes. These files are (1) a miscellaneous file, generally referred to as MISCFILE; (2) a configuration file, contained in the directory referenced by the files environment variable, generally referred to as AMPDSSYS; (3) a communications file, generally referred to as COMMFILE; and (4) an export file. Each of these four files is generally described as follows.

The miscellaneous file may be created using a file name of the CAD vendor's choice and set in an environment variable. This environment variable should contain the full path and file name of the miscellaneous file. Preferably, there should be separate miscellaneous files for each workstation on the system. Ideally, the miscellaneous files are located on the storage drive 101 of each workstation 100, rather than on a networked disk drive unit. In the present embodiment of the invention, the miscellaneous file contains information that is unique for each workstation in an installation. It contains the ID of the currently logged-on operator, a flag indicating if phone line ID numbers are used, the station number of the particular workstation 100 and a flag indicating if the expert medical dispatch software system is running in a resident mode or not.

The configuration file is a text file that contains several configuration parameters used by the expert medical dispatch software in a CAD environment. If any of the variables need to be set to non-default values, this file can be created or edited by a text editor in the sub-directory specified in the environment variables. Presently available variables for use in the configuration file include the following, each of which is identified with a brief description of its function. AllowReleaseToPend allows the user to release the call to pending and to return the program beck to CAD control. AllowOverride allows the operator to override to a higher response. AskGenderAgeOnUnk indicates that the user is always to obtain an age and gender. ExitOnDispatch sets the expert system to exit or pend on SEND events. AccessNoHiSublvls allows access to sub-levels other than those highlighted by the expert system recommendation. AllowMenuReconfig allows the Reconfigure Dispatch option. LogoffOnExit sets the system to always logoff the operator when the operator exits case entry. PollDelay is an integer value that represents the time in seconds that the expert system is to wait between polls of the communications file. PollCMode sets the communication file to close after every polling cycle or to leave the communication file open all of the time in a share mode or to close only when the status changes. PollFile provides the path and file name to poll the state of the current case instead of the communications file. CommFileMode can be set to (1) no CAD interface; (2) communication file is a disk file; (2) communication file is a named pipe; (3) communication file is a named message queue; (4) communication file is a DDE link; or (5) communication file is a TCP/IP socket. SignalCatch indicates whether when a signal is sent to case entry, a case in process will be aborted or if the signal will be ignored. AdjustCaseState indicates whether case states will be automatically adjusted to the correct value as necessary or whether an error will occur. ScreenDelay is an integer value that represents the timer value before the end of input is assumed on the entry of chief complaint numbers. ResponderScript indicates if the text from the responder script should be included in the COMMFILE. AllowProbDescPassed indicates whether CAD is to pass problem description text into the expert system. UpdatePassedCEfields allows the user to modify the location and callback fields in the expert system that have been passed from CAD, or keeps the user from modifying the location and callback fields in the expert system when they are passed from CAD. WriteCADonCEend causes the ProQA to update the COMMFILE with all available information when the user moves from Case Entry to Key Questions. AbortMode provides that when the operator aborts a case an abort DDE message is sent to CAD. AbortCADcode contains the returned string received by CAD in the CAD Incident Code field of the COMMFILE. AbortDispCode contains the returned string received by DAD in the Dispatch Level field of the COMMFILE. AllowAbortReason permits that the user can either type in free form text as a reason to abort a case or can only choose from the list of administrator defined abort reasons. AllowClose determines if the user can close the expert system through normal operating system conventions or must be shut down through CAD. AutoActivate permits the expert system to automatically change window states when the case state flag is set. AutoDeactivateDisp indicates whether the expert system will minimize itself on dispatch. AutoDeactivateClose indicates whether the expert system will minimize itself on case completion or will remain active on case completion. AutoNetLogin indicates if the network logon is used to automatically login to the expert system. Epoch specifies the current epoch for two-digit year entry. NotifyCADonStop indicates whether the COMMFILE should receive T state flag when the expert system is shutdown by the user. WriteCOMMFILEoninit indicates whether the COMMFILE will be rewritten when a case is initialized. WriteCOMMFILEonKQend if set causes the expert system to update the COMMFILE with all available information when the user moves from Key Questions to DLSs. FileAccessMode indicates whether database access is through a locally available file system or is via a TCP/IP to a database server. ServerName is a string value identifying the name of the database server. AutoPrintOnSend can be set to print selected case information when send or reconfigure occurs. AutoPrintOnClose can be set to print selected case information when the case is closed. AutoPrintSCaseInfo can be set print main case information. AutoPrintS4cmds can be sent to print the four commandments of the expert system. AutoPrintSDispInfo can be set to print dispatch information. AutoPrintSRespScr can be set to print the responder script. AutoPrintSTimeStamps can be set to print the time stamp information. AutoPrintSRunTimes can be set to print the running times. AutoPrintSKQs can be set to print the key questions of the expert system. AutoPrintSSeqs can be set to print the case sequences. AutoPrintSPrinter is set to the name of the printer to use when printing dispatch information on send. AutoPrintCCaseInfo can be set to print the main case information. AutoPrintC4cmds can be set to print the four commands of the expert system. AutoPrintCDispInfo can be set to print the dispatch information. AutoPrintCRespScr can be set to print the responder script. AutoPrintCTimeStamps can be set to print the time stamp information. AutoPrintCRunTimes can be set to print the running times. AutoPrintCKQs can be set to print the key questions. AutoPrintCSeqs can be set to print the case sequences. AutoPrintCPrinter is set to name the printer to use when printing dispatch information on closing a case. The communication file is the device by which CAD and the emergency dispatch expert system transfer information. Conceptually, the communication file is analogous to a shared memory segment in Unix with the first byte being a semaphore, controlling access to the rest of the memory/file. Preferably it should be a shared memory segment for speed and I-node use reasons, however, it can also be implemented as a file for portability with platforms that do not support inter-process communications. Since it is desirable to improve performance and to maintain multi-platform capability, the present implementation of this invention supports message queues and named pipes in Unix and DDE in Windows. The communication file may be created using a file name of the CAD vendor's choice and set in the environment variable COMMFILE. This variable would typically contain the full path and file name of the communication file. Preferably, the communication files are located on each workstation rather than a networked disk drive. The COMMFILE is presently treated as a sequential text file that contains alphanumeric and special punctuation or separator characters terminated by a new line character. Typically, the first line is a series of flags that indicate the presence or absence of subsequent lines and the status of the current case. The remaining lines contain data as indicated in the flags set in the first line. Presently the first line has thirty characters. The following table provides the present possible contents of each position and what that content means to the preferred emergency medical dispatch expert system. This is a bi-directional file, which is used to communicate between CAD and the expert system.

| Position | Description | Content | Meaning |
|---|---|---|---|
| 1** | State of the current case | | |
| | | I | Initialize CAD ⇒ ex sys |
| | | P | Pend ex sys ⇒ CAD |
| | | A | Abort ex sys ⇒ CAD |
| | | D | Dispatch ex sys ⇒ CAD |
| | | R | Reconfig. ex sys ⇒ CAD |
| | | C | Complete ex sys ⇒ CAD |
| | | O | Re-open CAD ⇒ ex sys |
| | | E* | Error ex sys ⇒ CAD |
| | | W* | Waiting CAD ⇒ ex sys |
| | | U* | Unpend CAD ⇒ ex sys |
| | | Q* | Quit CAD ⇒ ex sys |
| | | S* | Case Sum. CAD ⇒ ex sys |
| | | T* | Stopped ex sys ⇒ CAD |
| | | B* | Bring-top CAD ⇒ ex sys |
| | | M* | Case Entry finished message ex sys ⇒ CAD |
| | | K* | Key Question finished message ex sys ⇒ CAD |
| | | N* | New case # assigned ex sys ⇒ CAD |
| 2** | Operator number | Y | Operator no. specified |
| | | N | Operator no. not specif. |
| 3** | Incident number | Y | Incident no. specified |
| | | N | Incident no. not specif. |
| 4** | Location of incident | Y | Location of incident spec. |
| | | N | Location of incident not specified |
| 5** | Call back phone number | Y | Call back phone number specified |
| | | N | Call back phone number not specified |
| 6 | Problem (description) | Y | Problem specified |
| | | N | Problem not specified |
| 7 | Number of patients | Y | Number of patients specified |
| | | N | Number of patients not specified |
| 8 | Age (numerical) | Y | Age specified |
| | | N | Age not specified |
| 9 | Units of the age | Y | Units of age specified |
| | | N | Units of age not specif. |
| 10 | Sex of the patient | Y | Sex specified |
| | | N | Sex not specified |
| 11 | Is the patient conscious? | Y | Consciousness specified |
| | | N | Consciousness not specified |
| 12 | Is the patient breathing? | Y | breathing specified |
| | | N | breathing not specified |
| 13 | Chief complaint number | Y | Chief Complaint specif. |
| | | N | Chief Complaint not specified |
| 14 | Dispatch level | Y | Dispatch level specified |
| | | N | Dispatch level not specified |
| 15 | Reconfigured dispatch level | Y | Reconfigured dispatch level specified |
| | | N | Reconfigured dispatch level not specified |
| 16** | Export file name | Y | Export file name specif. |
| | | N | Export file name not specified |
| 17** | Call phone line number | Y | Call phone line no. specif. |
| | | N | Call phone line no. not specified |
| 18** | Override incident number | Y | Override incident number specified |
| | | N | Override incident number not specified |
| 19** | Return Information | Y | Return information specified |
| | | N | Return information not specified |
| 20** | Keystrokes to exit expert system | Y | Keystrokes to exit expert system specified |
| | | N | Keystrokes to exit expert system not specified |
| 21 | Keystroke ending session | Y | Keystroke ending session specified |
| | | N | Keystroke ending session not specified |
| 22 | Dispatch Level Suffix | Y | Dispatch level suffix specified |
| | | N | Dispatch level suffix not specified |
| 23 | Medical Response Text | Y | Medical response text specified |
| | | N | Medical response text not specified |
| 24 | Abort Text | Y | Abort text specified |
| | | N | Abort text not specified |
| 25 | Reevaluation | Y | Reevaluation specified |
| | | N | Reevaluation not specified |
| 26 | Exit Error Code | Y | Exit error code specified |
| | | N | Exit error code not specified |
| 27** | Post Send Dialog Message | Y | Post send dialog message flag specified |
| | | N | Post send dialog message flag not specified |
| 28 | CAD incident code | Y | CAD incident code specified |
| | | N | CAD incident code not specified |
| 29** | Automatic Case Complete | Y | Automatic case complete specified |
| | | N | Automatic case complete not specified |

-continued

| Position | Description | Content | Meaning |
|---|---|---|---|
| 30 | Responder Script | Y | Responder script specified |
| | | N | Responder script not specified. |

Below is an example of a communication file:
INYYYNNNNNNNNNNNNNNNNNNNNNNNNN
0093000001
1025 East Harrington Place
712-675-0098

The beginning "I" above indicates that this incident is being initialized. This flag is used to avoid a partially processed incident being passed to the expert system. When a new incident is started, the expert system is informed so that it does not attempt to access non-existent historical information. In initializing the resident version of the expert system, this flag will presently be set to "W," and all other flags will be set to "N." The second position is an "N" which indicates that no operator ID will be passed to the expert system. This means that the expert system will use the operator ID. If the miscellaneous file has "logged-out" as the operator and no operator ID is passed to the expert system, through the COMMFILE, or the operator ID is invalid, an error will occur. Each valid operator ID passed in the COMMFILE will update the miscellaneous file automatically so that the miscellaneous file will contain the most recently used operator ID. Each new operator ID passed in the COMMFILE will be added to the operator database on the first reference. Positions three through five are "Y"'s. This indicates that an incident number, location and call back number will be expected in the communication file on the second, third and fourth lines. The rest of the top line contains "N"'s. This means that no other information will be passed in the communication file. Not all of the possible information needs to be exchanged each time. It is up to the CAD vendor to decide what information is important for them to share with the expert system. Only those items marked with "*" in the table above should be passed by CAD through the COMMFILE to the expert system. It is suggested that the location and call back number always be exchanged.

The limitations on the type of data stored in each fields (or lines) is described in the table below. In the present embodiment, all alpha characters are converted to upper case by the preferred expert system.

| Line | Description | Length or possible content1 |
|---|---|---|
| 1. | State/Flags | 30 characters |
| 2. | Operator number | 1 to 10 alphanumeric characters specifying the operator ID on file with expert system |
| 3. | Incident number | 1 to 10 alphanumeric characters specifying the case number. |
| 4. | Location of incident | 1 to 60 alphanumeric characters |
| 5. | Call back phone number | 1 to 20 numeric and punctuation characters |
| 6. | Problem description | 1–40 alphanumeric characters |
| 7. | Number of patients | Numeric characters ranging 1 to 127 or the text "UNKNOWN" |
| 8. | Age | Numeric characters ranging 1 to 127 or an "age range" description |

-continued

| Line | Description | Length or possible content1 |
|---|---|---|
| 9. | Units of the age | Description of the contents of the "Age" field, i.e., years, months or range |
| 10. | Sex of patient | Description of patient "" gender; i.e., MALE, FEMALE, UNKNOWN |
| 11. | Is the patient conscious? | Description of patient's state of consciousness; i.e., YES, NO, UNKNOWN |
| 12. | Is the patient breathing? | Description of patient's state of breathing; i.e., YES, NO, UNCERTAIN, UNKNOWN |
| 13. | Chief complaint number | Numeric characters ranging 1 to 32 |
| 14. | Dispatch level | Special format |
| 15. | Reconfigure dispatch level | Special format |
| 16. | Export file name | 1 to 80 legal file name characters |
| 17. | Phone line number | 1 to 4 alphanumeric characters |
| 18. | Override incident number | 1 to 10 alphanumeric characters, which will change the current case number, assigned. |
| 19. | Return information | String of "Y"s and "N"s indicating which fields should be returned to the CAD system in the communication file. |
| 20. | Keystrokes to exit expert system | List of keystrokes used to exit expert system. These are in a two-character format. |
| 21. | Keystroke which ended session | A two-character field showing which keystroke was used to exit the expert system. |
| 22. | Dispatch level suffix | Only applicable on chief complaint numbers 4, 23 and 27. |
| 23. | Medical response text | The actual text of the response as it appears on the key question screen. |
| 24. | Abort text | The actual text of the reason for aborting the case. |
| 25. | Reevaluation | A "Y" or "N" indicating whether to allow reevaluation or not. |
| 26. | Exit error code | The code number of the error, which caused the expert system to terminate. |
| 27. | Post send dialog message | "Y" or "N" indicating whether or not a dialog box should appear on the screen after a send or reconfigure, and prior to an automatic jump to Pre-Arrival Instructions. |
| 28. | CAD incident code | Returns the CAD incident code for the dispatch determinant, if it exists in the user-defined responses. |
| 29. | Automatic case complete | I set to "Y" the expert system performs a case complete without any further action by the operator. |
| 30. | Responder script | Returns human readable text describing the sit situation. |

The communications file, in the present preferred embodiment, is handled differently depending on whether the invention is operating in the non-resident mode or the resident mode.

Figure 2A:
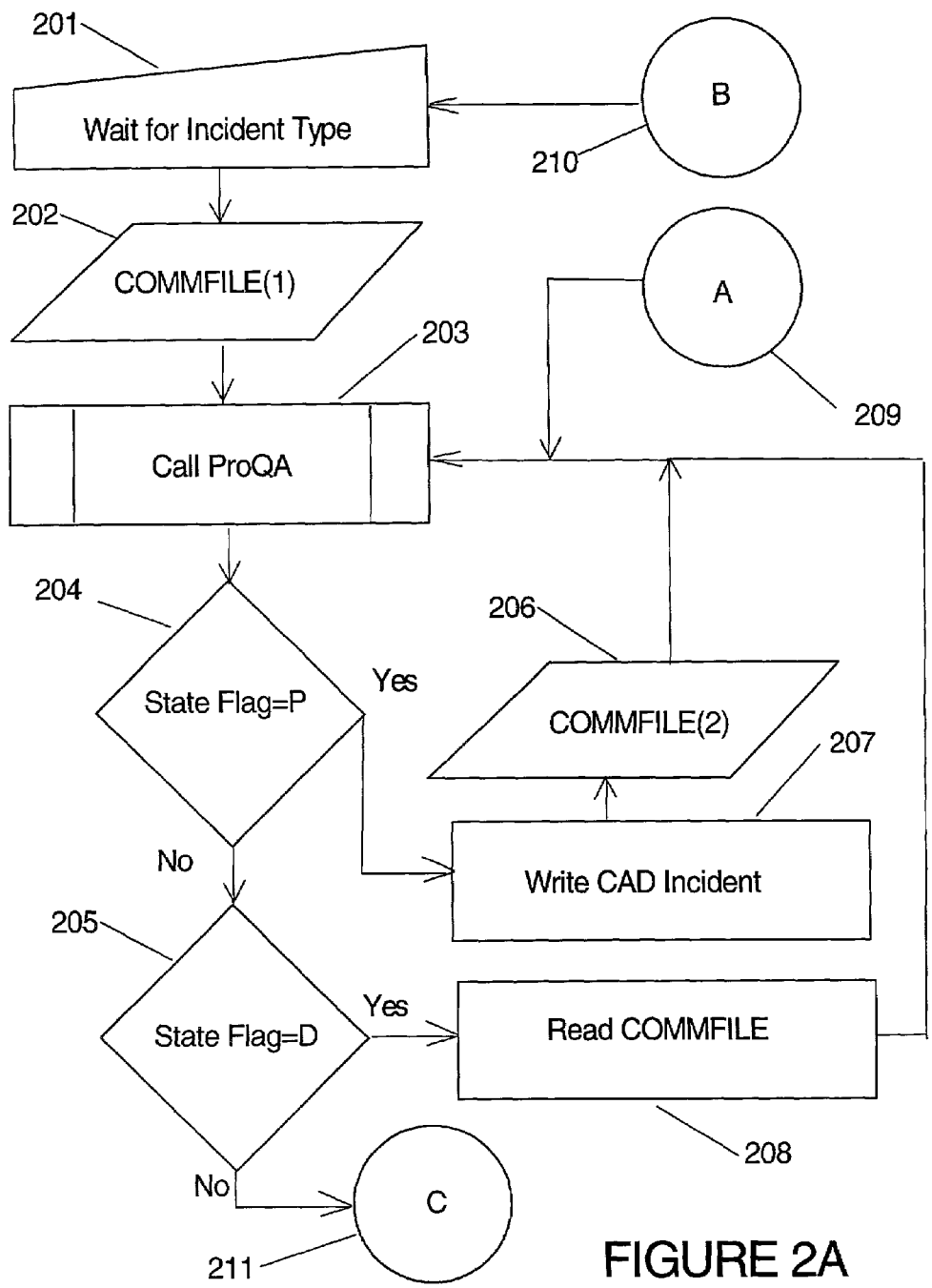
FIGS. 2a and 2b are flow diagrams of the preferred steps of the non-resident mode integration process of this invention.
Figure 2B:
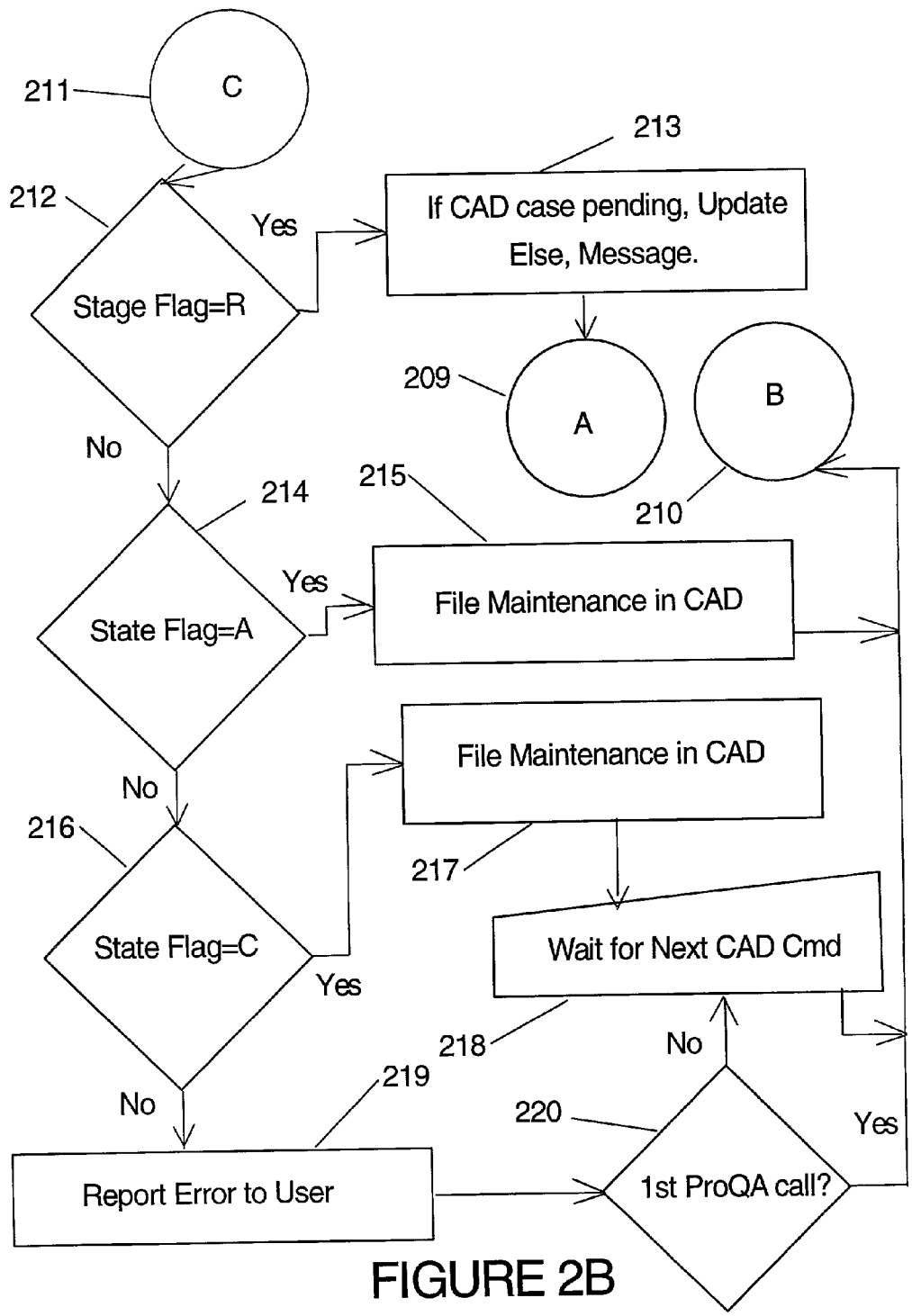

FIGS. 2a and 2b are flow diagrams of the preferred steps of the non-resident mode integration process of this invention. The non-resident mode is specified when the fourth line of the miscellaneous file is set to "N." This allows a single thread of execution to be used for each dispatch workstation. Initially, the process waits for an incident type 201. When an incident type 201 occurs, CAD writes 202 to the COMMFILE the initial information to start a case. In the present embodiment, this means writing a line that has an "I" in the first position, four "Y"'s and finally 25 "N"'s Following this line, there should be four more lines containing the operator ID, incident number, location and call back number. Optionally, fields 16, 17, 19 and/or 20 may be specified if CAD will use these features. The expert system is then called 203 to perform its interrogation. When control is returned to CAD, the state flag will be set to "P," "D," "R," "A," "C," or "E". A state flag=P test 204 is made to determine if the operator selected the Release to pending option from the expert system menu. If the state flag is equal to P, the CAD incident is written 207 to a pending COMMFILE 206 and is returned to the CAD's normal stand-by/waiting for the next command mode by again calling the expert system 203. If the state flag is not equal to P then a state flag D test 205 is made to determine if the expert system has recommended that a dispatch should occur and has returned the applicable information in fields 22, 23 and 28. If the state flag is equal to D, the CAD program, preferably and typically, reads 208 the COMMFILE for these three fields and either allows the user to dispatch the incident or place the call with the recommended call type in the CAD's pending file for another operator to pick up and dispatch, depending on whether the CAD is using horizontal or vertical dispatching methods. In either case, when CAD is finished, the process of this invention returns to the expert system 203. This completes the preferred medical protocols of the expert system. At a minimum, post-dispatch instructions will typically be given and there may be further questions that need to be asked to construct a complete pIcture of what is happening in the field. Moreover, sometimes pre-arrival instructions will need to be given. If the state flag is not equal to D, the process goes to transition step C 211 in FIG. 2B. In FIG. 2B transition step C 211 takes the processto a state flag=R test 212, which if true indicates that because of additional information that the expert system has changed the recommended dispatch level. Typically, the R flag is returned only after the expert system has returned at least one time with a "D" state flag. If the previously pending case is still pending, CAD updates 213 the dispatch level and recalls the expert system 203 via transition step A 209 to FIG. 2A. If the case has already been retrieved by another dispatcher or if the current user performed a dispatch initially, appropriate measures need to be taken to change the level of response in CAD. Again, after this process is complete, the expert system is recalled 203, via transition step A 209 to FIG. 2A. If the state flag is not equal to R, then the state flag=A test 214 is made to determine if the user has aborted the case. This would only be expected to occur prior to a dispatch of emergency medical assistance. Therefore, CAD will typically perform any file maintenance 215 that is required and return the user to the incident type entry 201 of FIG. 2A via transition step B 210. If the state flag does not equal A, then a state flag=C test 216 is made to determine if the case has been completed as fat as the expert system is concerned. If the case has been completed, then CAD performs any necessary file maintenance 217 and wait 218 for the next CAD command, that is, the process goes into a normal stand-by mode. If the state flag is not equal to C, then an error has occurred, which is reported 219 to the user. A test 220 as to whether the expert system initialized the case is made. If it did not, then the normal stand-by mode is entered 218. If the expert system did initialize the case, CAD returns to the wait for incident type step 201, shown via transition step B 210 to FIG. 2A.

Figure 3:
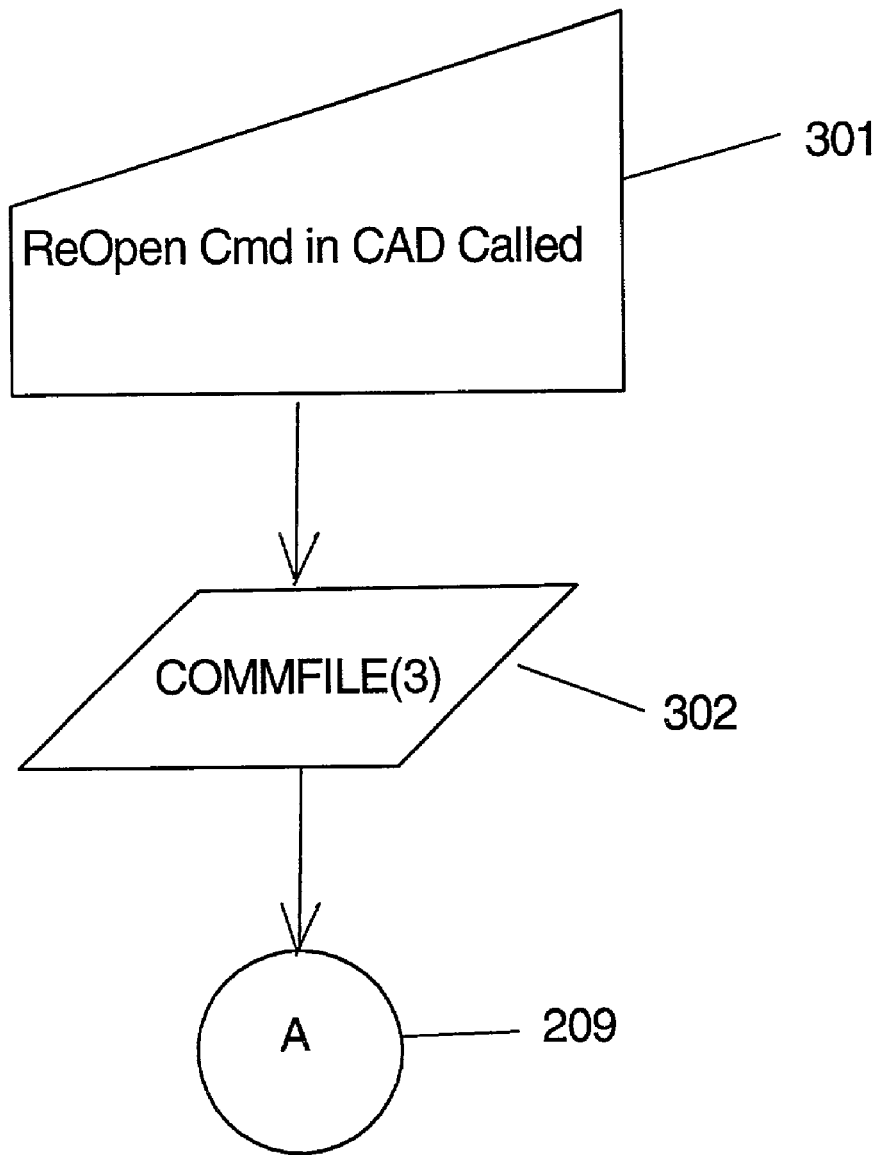
FIG. 3 is a flow diagram of the preferred reopen procedure of this invention.

FIG. 3 shows a flow diagram of the preferred reopen procedure of this invention. In addition to the standard process described above in reference to FIGS. 2A and 2B, the present embodiment of this invention also provides CAD with the option of reopening a case that has been completed or aborted and can get a case summary of any case. Essentially, similar to initially calling the expert system, except that instead of using an "I" to initialize the case, and "O" is used to indicate to the expert system that the case is already on file and to reopen 301 the case retrieving the information from its historical database. As shown in this FIG. 3, in the present embodiment only two fields are required to open the case in the communication file 302, the operator ID and the incident number. While the minimum requirement to reopen a case is the incident number, it is desirable to use the operator ID also to ensure accurate historical information. In addition to these fields, the location, callback number and/or problem description may also be passed on the appropriate lines, thereby updating with new values the historical database. Return processing from the expert system is the same as described above, hence the connector symbol for transition step A 209 is provided returning the process to FIG. 2A. If the expert system has pended a case, generally at some point in time CAD will need to retrieve the case and continue processing. Retrieving the case and continuing processing is performed in essentially the same manner as reopen of this FIG. 3, with the difference being the a "P" is written in the first byte instead of a "O".

Figure 4:
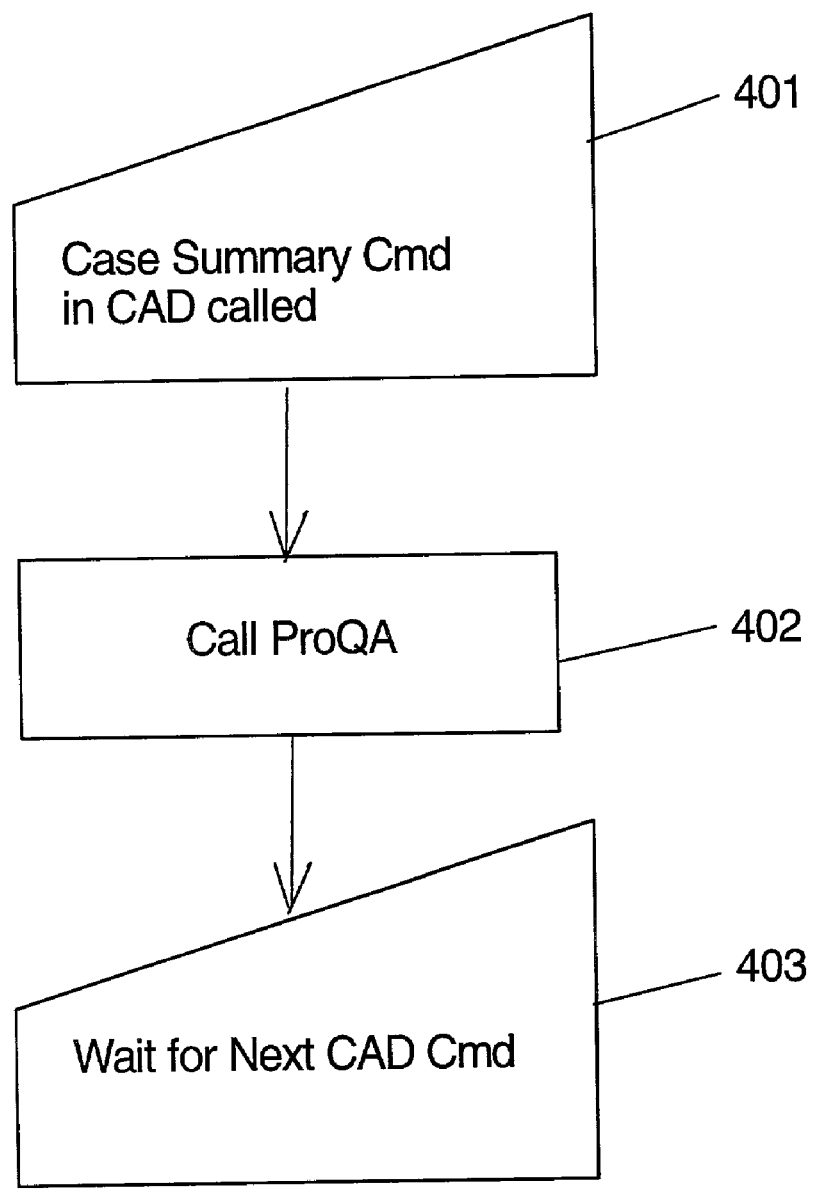
FIG. 4 is a flow diagram of the preferred case summary procedure of this invention.

FIG. 4 shows a flow diagram of the preferred case summary procedure of this invention. In the present preferred embodiment of this invention, a user may display a case summary at nearly any time during the processing of a case. CAD may provide this functionality as a separate CAD command or menu item. As shown in this FIG. 4, initially the case summary command in CAD is called 401. The expert system is then called 402 to collect the case summary information. Typically the case is identified by passing the case number to the expert system. Lastly, the process waits 403 for the next CAD command.

Figure 5:
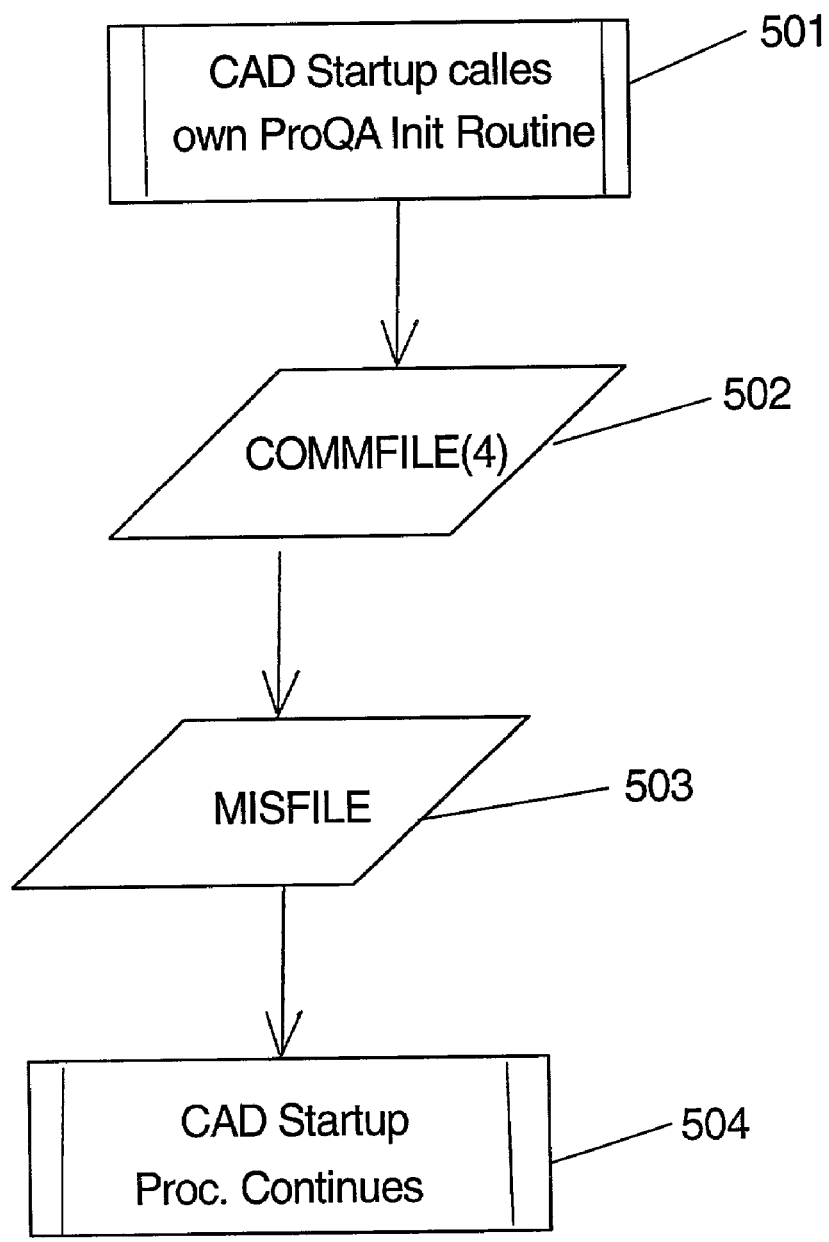
FIG. 5 is a flow diagram of the preferred startup procedure of this invention.
Figure 7A:
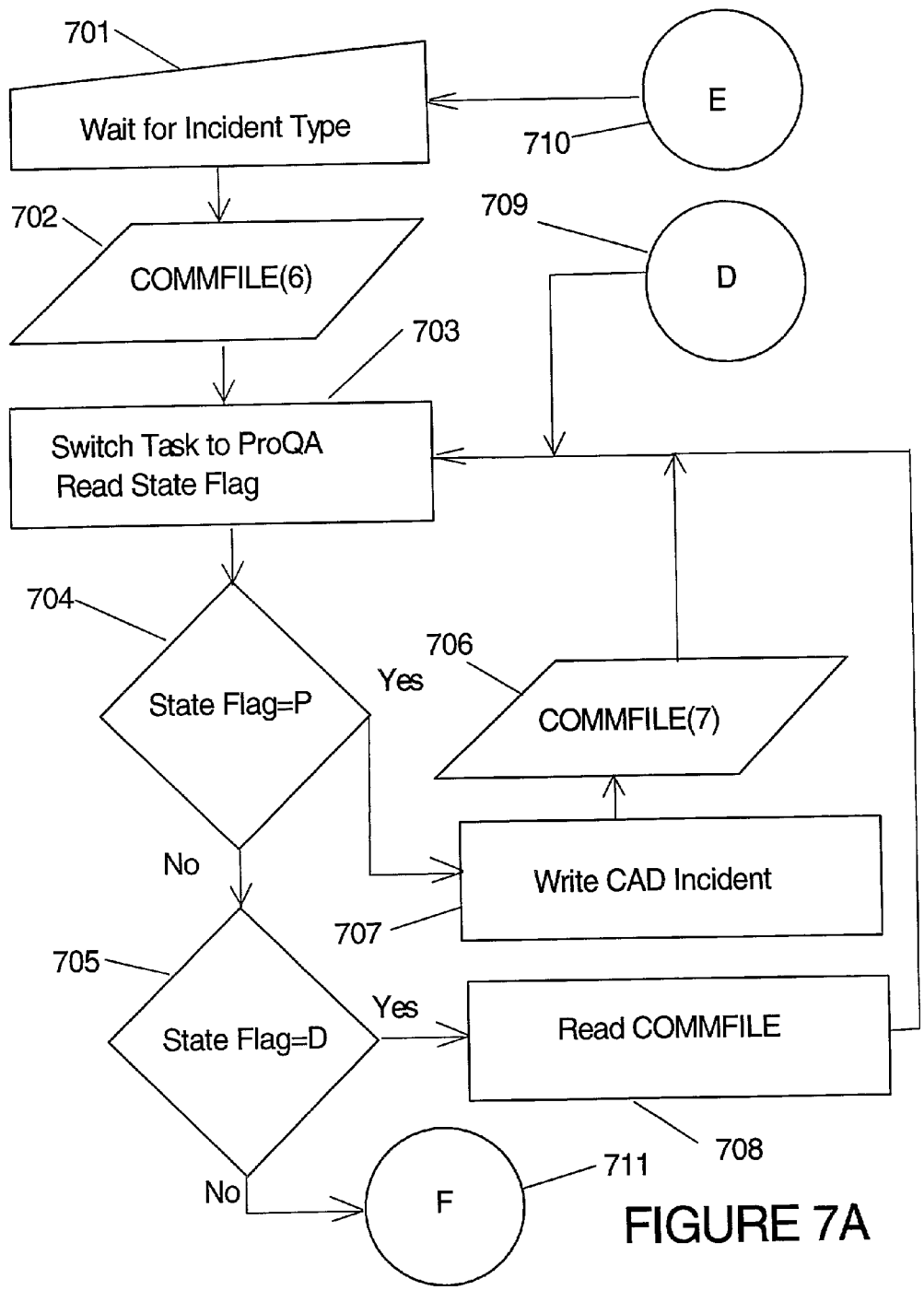
FIGS. 7a and 7b are flow diagrams of the preferred steps of the resident mode integration process of this invention.
Figure 7B:
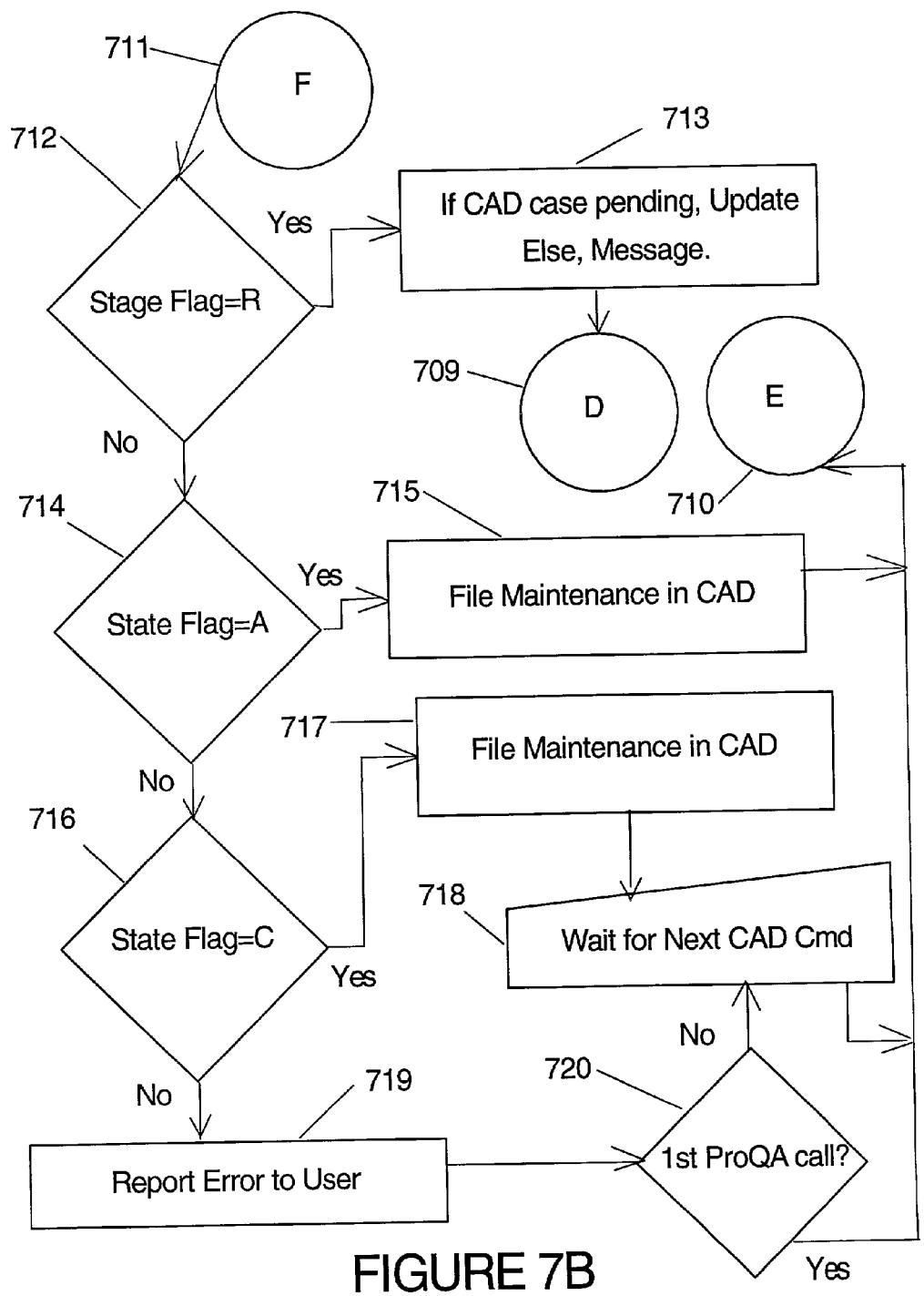

FIG. 5 shows a flow diagram of the preferred startup procedure of this invention when operating in the resident mode. In the present embodiment resident mode is specified when the fourth line of the miscellaneous file is set to "Y." This approach permits the use of a multiple thread execution for each dispatch workstation; one for dispatch and another for the expert system. Additional detail on the interaction of CAD with the expert system when the invention is operating in resident mode is shown in FIGS. 7A and 7B. When CAD executes its startup procedure it will typically initialize 501 the miscellaneous file 503 and the communication file 502 with default startup values. The first line of the miscellaneous file is set to "logged out." While the second and third lines are set as appropriate for the installation, as previously described. The last line of the miscellaneous file is set to "Y" to indicate resident mode operation. The communication file will consist of a single line containing a "W" as the state flag and a series of "N"'s in the remaining positions. The CAD startup process then continues normally and the expert system is started as a separate task 504.

Figure 6:
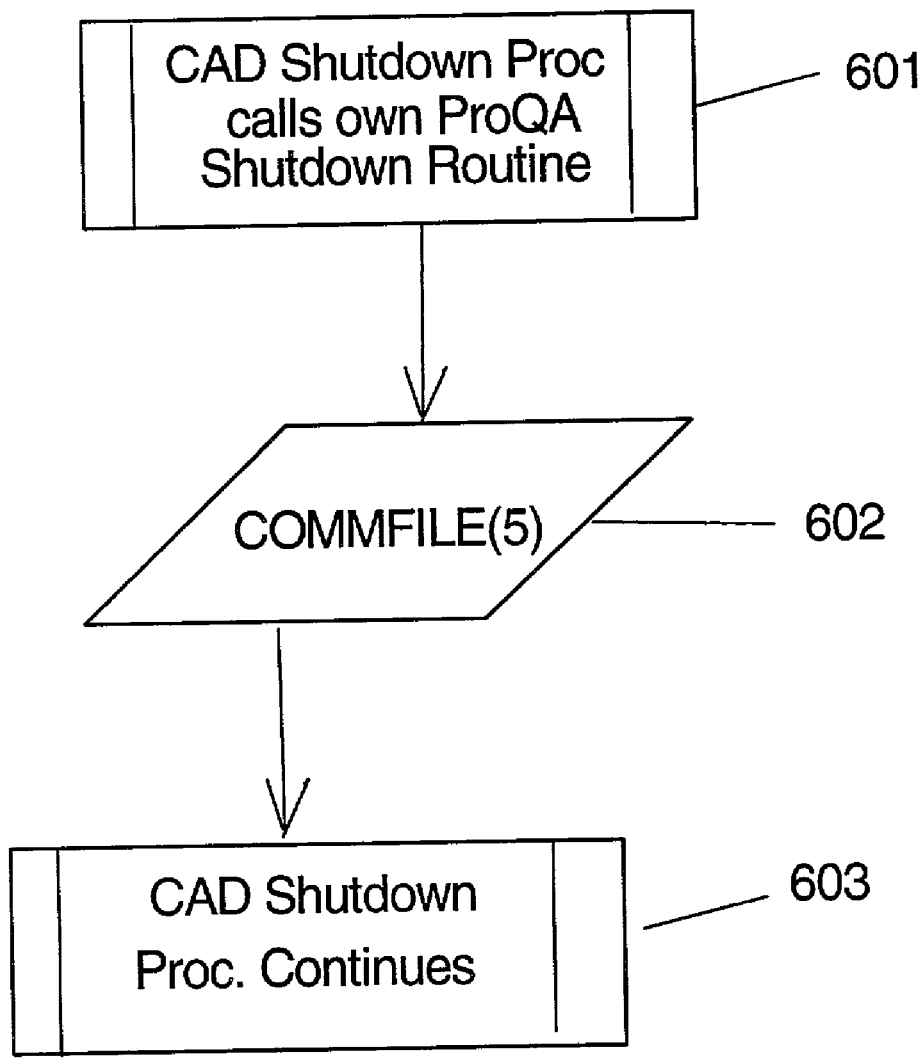
FIG. 6 is a flow diagram of the preferred shutdown procedure of this invention.

FIG. 6 shows a flow diagram of the preferred shutdown procedure of this invention. When CAD exits the shutdown process is similar to the process as previously described. The CAD shutdown process calls the expert system shutdown routine 601. CAD writes 602 a "Q" to the state flag in the communication file. When the expert system reads the "Q" it will shut itself down 603. In the present embodiment of the invention, the expert system will not shutdown the shell environment that it is running within, so that either a batch/shell script will typically be set-up to perform initialization and exiting of the operating system resources or CAD will perform the initialization and exiting under its own control.

FIGS. 7a and 7b are flow diagrams of the preferred steps of the resident mode integration process of this invention. In many ways processing a case in resident mode is very similar to the non-resident mode. Just as in non-resident mode, CAD is typically configured such that when CAD is waiting 701 for an incident type, the user can specify entry into the expertsystem (ProQA). by a key press or specific code entry. When this action occurs, CAD writes 702 to the communication file (COMMFILE) the initial information to start the case. Unlike non-resident mode, in resident mode, this means writing a line that has a "W"' in the first position, usually and typically followed by four "Y"'s and finally followed by 25 "N"'s. Typically, following this line there will be four more lines containing the operator ID. incident number, location and callback number. Optionally, fields 16, 17, 19 and/or 20 may be specified if CAD can use these features. After the communication file 702 has all of the required information, then an "I" is written to the first position. The expert system is then called which polls and continues to poll for changes In the state flag, which will then detect the new information, read the communication file and begin processing. Typically, CAD meanwhile begins reading the state flag of the communication file (COMMFILE) looking for a change from "I" to another value. In resident mode, expert system continuously polls the case state flag. As indicated above, the process initially waits for an incident type 701. When an incident type 701 occurs, CAD writes 702 to the COMMFILE the initial information to start a case In this resident mode embodiment, this means writing a line that has an "'W" in the first position, four "Y"'s and finally 25 "N"'s. The expert system is then called 703 to perform its interrogation. When control is returned to CAD, the state flag will be set to "P," "D," "R," "A," "C," or "E". A state flag=P test 704 is made to determine if the Allow-ReleaseToPend is set to its sefault value of Yes, indicating that the operator selected the Release to pending option from the expert system menu. If the state flag is equal to P, the CAD incident is written 707 to a pending COMMFILE 706 and is returned to the CAD's normal stand-by/waiting for the next command mode by again continuing to poll for changes in the state flag 703. After the expert system has pended a case, at some point in time CAD will retrieve the case and will continue processing. This is essentially the same as the reopen option with the exception that a "U" is written to the first byte rather than an "O". If the state flag is not equal to P then a state flag D test 705 is made to determine if the expert system has recommended that a dispatch should occur and has returned the applicable information in fields 22, 23 and 28. If the state flag is equal to D, the CAD program, preferably and typically, reads 708 the COMMFILE for these three fields and either allows the user to dispatch the incident or place the call with the recommended call type in the CAD's pending file for another operator to pick up and dispatch, depending on whether the CAD is using horizontal or vertical dispatching methods. In either case, when CAD is finished, thQ process of this invention returns to pol5ng the communication file 703. This completes the preferred medical protocols of the expert system. At a minimum, post-dispatch instructions will typically be given and there may be further questions that need to be asked to construct a complete picture of what is happening in the field. Moreover. sometimes pre-arrival instructions will need to be given. If the state flag is not equal to D, the process goes to transition step F 711 in FIG. 7B. In FIG. 7B transition step F 711 takes the process to a state flag=R test 712, which if true indicates that because of additional information that the expert system has changed the recommended dispatch level. Typically, the R flag is returned only after the expert system has returned at least one time with a "D" state flag. If the previously pending case is still pending, CAD updates 713 the dispatch level and continue checking the communication file for further changes 703 via transition step D 709 to FIG. 7A. If the case has already been retrieved by another dispatcher or if the current user performed a dispatch initially, appropriate measures need to be taken to change the level of response in CAD. Again, after this process is complete, the CAD should again continue checking the communication rde for further changes 703, via transition step D 709 to FIG. 7A. If the state flag is not equal to R, then the state flag=A test 714 is made to determine if the user has aborted the case. This would only be expected to occur prior to a dispatch of emergency medical assistance. Therefore, CAD will typically perform any file maintenance 715 that is required and return the user to the incident type entry 701 of FIG. 7A via transition step E 710. If the state flag does not equal A, then a state fag=C test 716 is made to determine if the case has been completed as far as the expert system is concerned. If the case has been completed, then CAD performs any necessary file maintenance 717 and wait 718 for the next CAD command, that is, the process goes into a normal stand-by mode. If the state flag is not equal to C, then an error has occurred, which is reported 719 to the user. A test 720 as to whether the expert system initialized the case is made. If it did not, then the normal stand-by mode is entered 718. If the expert system did initialize the case, CAD returns to wait for incident type step 701, shown via transition step E 710 to FIG. 7A.

The resident mode has the same option to reopen as non-resident mode and works basically in the same manner. As with typical case processing, the difference between non-resident mode and resident mode is that in resident mode rather than calling the expert system after writing to the communication file, the CAD process goes into a polling mode to detect a change in the state flag.

Figure 8:
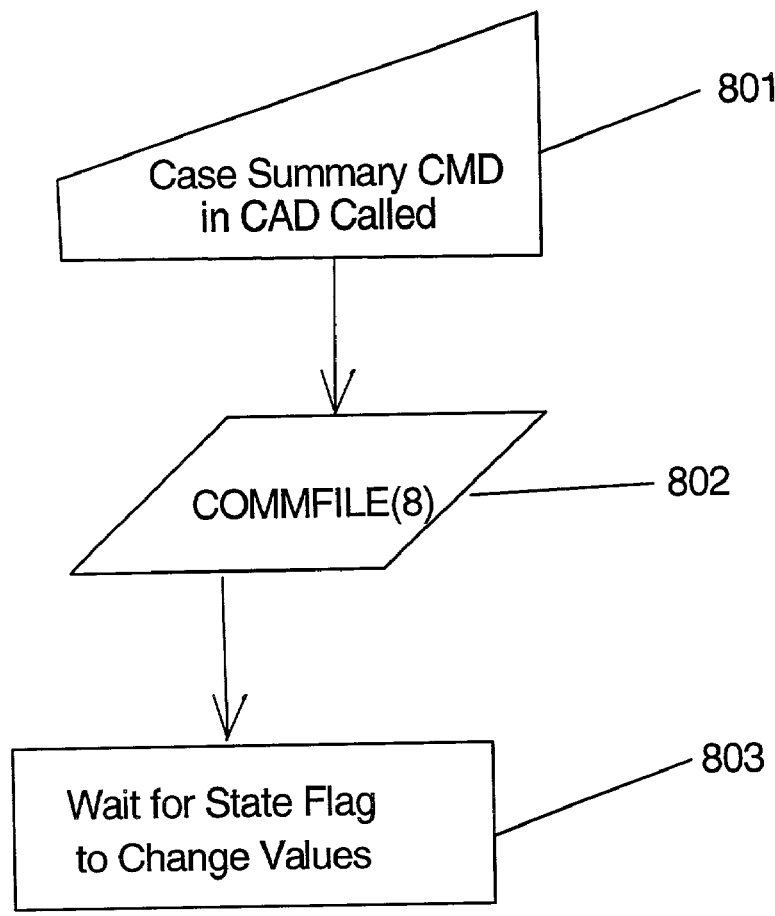
FIG. 8 is a flow diagram of the preferred case summary procedure of this invention.

FIG. 8 shows a flow diagram of the preferred case summary procedure of this invention. As in resident mode, there are two options for displaying Case Summary information: (1) it can be done the same as in non-resident mode where the expert system is called with a command line argument in the CAD environment's thread of execution; or (2) can be used that is more like the reopen option. The reopen option is shown in this FIG. 8. The case summary command in CAD is called 801, following which the communication file is passed a "S" state flag 802 along with the incident number and then CAD waits 803 for a change in the state flag.

The previous described preferred embodiments of the invention are to be considered in all respects only as illustrative and not as restrictive. Although the embodiments shown describe particular components in particular connection configurations, the invention is not limited thereto. The scope of this invention is indicated by the appended claims rather than by the foregoing description. All systems and devices, which come directly within the claims or within the meaning and range of equivalency of the claims, are to be embraced as being within the scope of protection of this invention.

The invention claimed is:

1. A method for integrating a computer aided dispatch system and an emergency medical dispatch protocol, comprising:
   (A) initiating a computer aided dispatch system;
   (B) receiving an incident call;
   (C) calling an expert emergency medical dispatch system, said expert emergency medical dispatch system interrogating for information; calculating a determinate value based on said information; and setting a dispatch process state for use by said computer aided dispatch system;
   (D) returning control to said computer aided dispatch system, said computer aided dispatch system testing for said desired dispatch process states, wherein said dispatch process states provide a control for the operation of said computer aided dispatch system; and
   (E) returning control to said expert emergency medical dispatch system.

2. A method for integrating a computer aided dispatch system and an emergency medical dispatch protocol, as recited in claim 1, further comprising writing a computer aided dispatch incident to a communication file.

3. A method for integrating a computer aided dispatch system and an emergency medical dispatch protocol, as recited in claim 1, further comprising reporting errors to a user.

4. A method for integrating a computer aided dispatch system and an emergency medical dispatch protocol, as recited in claim 1, wherein said testing for desired process states fwlher comprises testing if an operator has selected a release to pending option.

5. A method for integrating a computer aided dispatch system and an emergency medical dispatch protocol, as recited in claim 1, wherein said testing for desired process states further comprises testing if an operator of said computer aided dispatch system needs to retrieve a case.

6. A method for integrating a computer aided dispatch system and an emergency medical dispatch protocol, as recited in claim 1, wherein said testing for desired process states further comprises testing whether said expert emergency medical dispatch system has recommended that a dispatch should occur.

7. A method for integrating a computer aided dispatch system and an emergency medical dispatch protocol, as recited in claim 1, wherein said testing for desired process states further comprises testing whether said expert emergency medical dispatch system has changed a recommended dispatch level.

8. A method for integrating a computer aided dispatch system and an emergency medical dispatch protocol, as recited in claim 1, wherein said testing for desired process states further comprises testing whether a user has aborted a case.

9. A method for integrating a computer aided dispatch system and an emergency medical dispatch protocol, as recited in claim 1, wherein said testing for desired process states further comprises testing whether a case has been completed.

10. A method for integrating a computer aided dispatch system and an emergency medical dispatch protocol, as recited in claim 1, wherein said testing for desired process states further comprises testing whether an error has occurred.

11. A system for integrating a computer aided dispatch system and an emergency medical dispatch protocol, comprising:
    (A) a computer device; and
    (B) a computer program operating on said computer device, wherein said computer program further comprises:
       (1) an operating system, managing the operation of said computer device;
       (2) a computer aided dispatch system operating in cooperation with said operating system to manage emergency response resources;
       (3) an emergency medical response protocol system for guiding a dispatcher's response to a caller, wherein said emergency medical response protocol system further comprises a set of specified inquiries, a calculated determinate value based one or more responses to said set of specified inquiries, and a defined emergency medical response based on said determinate value; and
       (4) an interface between said computer aided dispatch system and said emergency medical response protocol system, wherein said interface is a process for communicating information between said computer aided dispatch system and said emergency medical response protocol system, wherein said interface further comprises a miscellaneous file containing information unique to a workstation; a configuration file containing configuration variables; a communication file which is a bidirectional file for use in communicating data between said computer aided dispatch system and said emergency medical response protocol system, a set of state flags set by said emergency medical response protocol system and detected by said computer aided dispatch system to control operation of said computer aided dispatch system; and an export file.

12. A system for integrating a computer aided dispatch system and an emergency medical dispatch protocol, as recited in claim 11, wherein said computer device further comprises:
    (1) a processor, wherein said processor is capable of opelating both a computer aided dispatch system and an emergency medical response protocol system;
    (2) a memory unit in electronic communication with said processor;
    (3) a display device in electronic communication with said processor; and
    (4) an input device in electronic communication with said processor.

13. A system for integrating a computer aided dispatch system and an emergency medical dispatch protocol, as recited in claim 11, wherein said operating system is selected from the group consisting of MS-DOS, Windows, Unix, AIX, CLIX, QNX, OS/2, and Apple.

14. A system for integrating a computer aided dispatch system and an emergency medical dispatch protocol, as recited in claim 11, wherein said interface further comprises a method comprising:
    (a) initiating a computer aided dispatch system;
    (b) receiving an incident call;
    (c) calling an expert emergency medical dispatch system, said expert emergency medical dispatch system setting one or more desired process states;
    (d) returning to said computer aided dispatch system, said computer aided dispatch system testing for said one or more desired process states; and
    (e) returning control to said expert emergency medical dispatch system.

* * * * *

UNITED STATES PATENT AND TRADEMARK OFFICE
CERTIFICATE OF CORRECTION

| | |
|---|---|
| PATENT NO. | : 7,106,835 B2 |
| APPLICATION NO. | : 10/124786 |
| DATED | : September 12, 2006 |
| INVENTOR(S) | : Richard Saalsaa |

It is certified that error appears in the above-identified patent and that said Letters Patent is hereby corrected as shown below:

Column 2, line 65, "...FIGS. 2*a* and 2*b* are flow diagrams..." change to -- FIGS. 2A and 2B are flow diagrams --

Column 3, line 9, "...FIGS. 7*a* and 7*b* are flow diagrams..." change to -- FIGS. 7A and 7B are flow diagrams --

Column 4, line 41, "...place the call "on hold" and return a later time." change to -- place the call "on hold" and return at a later time. --

Column 4, line 59, "...instructions and inquiries; an user input device..." change to -- instructions and inquiries; a user input device --

Column 4, line 64, "...the invention, run under the following..." change to -- the invention run under the following --

Column 4, line 64, "...run under the following operating systems MS-DOS..." change to -- run under the following operating systems: MS-DOS --

Column 5, line 33, "...and to return the program beck to CAD..." change to -- and to return the program back to CAD --

Column 6, line 10, "...string received by DAD in the Dispatch..." change to -- string received by CAD in the Dispatch --

Column 6, line 27, "...by the user. WriteCOMMFILEoninit indicates..." change to -- by the user. WriteCOMMFILEonInit indicates --

Column 6, line 39, "...can be set print main case..." change to -- can be set to print main case --

Column 6, line 40, "...can be sent to print the main..." change to -- can be set to print the main --

Column 9, line 46, "...type of data stored in each fields (or lines) is..." change to -- type of data stored in the fields (or lines) is --

Column 9, line 53, "...Length of possible content1 ..." change to -- Length of possible content --

UNITED STATES PATENT AND TRADEMARK OFFICE
CERTIFICATE OF CORRECTION

PATENT NO. : 7,106,835 B2
APPLICATION NO. : 10/124786
DATED : September 12, 2006
INVENTOR(S) : Richard Saalsaa It is certified that error appears in the above-identified patent and that said Letters Patent is hereby corrected as shown below:

Column 10, line 4, "...Length of possible content1 ..." change to -- Length of possible content --

Column 10, line 7, "...Description of patient "" gender;..." change to -- Description of patient "gender;" --

Column 10, line 7, "...Description of patient "gender;" i i.e., Male,..." change to -- Description of "patient's gender;" i.e., Male, --

Column 10, line 16, "...15. Reconfigure dispatch level..." change to -- 15. Reconfigured dispatch level --

Column 10, line 54, "...I set to "Y" the expert system..." change to -- If set to "Y" the expert system --

Column 10, line 59, "...describing the sit situation." change to -- describing the situation. --

Column 10, line 66, "...FIGS. 2*a* and 2*b* are flow diagrams..." change to -- FIGS. 2*A* and 2*B* are flow diagrams --

Column 11, line 8, "...four "Y"'s and finally 25 "N"'s ..." change to -- four "Y"'s and finally 25 "N"'s --

Column 11, line 11, "...fields 16, 17, 18 and/or 20 may be specified..." change to -- fields 16, 17, 18, and/or 20 may be specified --

Column 11, line 14, "...be set to "P," "D," "R," "A," "C,"..." change to -- be set to "P," "D," "PTO," "R," "A," "C," --

Column 11, line 24, "...in fields 22, 23 and 28. If the..." change to -- in fields 22, 23 and 28. If the --

Column 11, line 36, "...construct a complete picture of what is..." change to -- construct a complete picture of what is --

Column 11, line 40, "...takes the processto a state flag..." change to -- takes the process to a state flag --

UNITED STATES PATENT AND TRADEMARK OFFICE
CERTIFICATE OF CORRECTION

PATENT NO.       : 7,106,835 B2
APPLICATION NO.  : 10/124786
DATED            : September 12, 2006
INVENTOR(S)      : Richard Saalsaa It is certified that error appears in the above-identified patent and that said Letters Patent is hereby corrected as shown below:

Column 11, line 42, "...additional information that the expert..." change to -- additional information the expert --

Column 11, line 61, "...been completed as fat as the expert..." change to -- been completed as far as the expert --

Column 11, line 63, "...maintenance 217 and wait 218 for the..." change to -- maintenance 217 and waits 218 for the --

Column 12, line 11, "...Essentially, similar to initially calling..." change to -- Essentially, it is similar to initially calling --

Column 12, line 12, "...initialize the case, and "O" is used to..." change to -- initialize the case, an "O" is used to --

Column 12, line 31, "...the same manner as reopen of this..." change to -- the same manner as the reopen of this --

Column 12, line 32, "...difference being the a "P" is written..." change to -- difference being that a "P" is written --

Column 12, line 33, "...byte instead of a "O"." change to -- byte instead of an "O". --

Column 12, line 57, "...set to "logged out." While the second and third..." change to -- set to "logged out". The second and third --

Column 13, line 11, "...FIGS. 7*a* and 7*b* are flow diagrams..." change to -- FIGS. 7*A* and 7*B* are flow diagrams --

Column 13, line 17, "...into the expertsystem (ProQA). by a..." change to -- into the expert system (ProQA), by a --

Column 13, line 17, "...into the expert system (ProQA). by a..." change to -- into the expert system (ProQA), by a--

Column 13, line 21, "...a line that has a "W"" in the..." change to -- a line that has a "W" in the --

UNITED STATES PATENT AND TRADEMARK OFFICE
CERTIFICATE OF CORRECTION

PATENT NO. : 7,106,835 B2
APPLICATION NO. : 10/124786
DATED : September 12, 2006
INVENTOR(S) : Richard Saalsaa It is certified that error appears in the above-identified patent and that said Letters Patent is hereby corrected as shown below:

Column 13, line 23, "...followed by 25 "N"'s." change to -- followed by 25 "N"'s --

Column 13, line 24, "...containing the operator ID. incident..." change to -- contain the operator ID, incident --

Column 13, line 25-26, "...fields 16, 17, 19, and/or 20 may be..." change to -- fields 16, 17, 19, and/or 20 may be --

Column 13, line 30, "...to poll for changes In the state..." change to -- to poll for changes in the state --

Column 13, line 39, "...to start a case In this..." change to -- to start a case. In this --

Column 13, line 40, "...that has an ""W" in the..." change to -- that has a ""W" in the --

Column 13, line 40, "...that has a ""W" in the..." change to -- that has a "W" in the --

Column 13, line 41, "...and finally 25 "N"'s." change to -- and finally 25 "N"'s --

Column 13, line 42, "...control is retumed to CAD, the..." change to -- control is returned to CAD, the --

Column 13, line 44, "...to its seafault value of Yes, indicating..." change to -- to its default value of Yes, indicating --

Column 13, line 48, "...and is returned to the CAD's..." change to -- and is returned to the CAD's --

Column 13, line 57, "...in fields 22, 23 and 28. If..." change to -- in fields 22, 23 and 28. If --

Column 13, line 64, "...CAD is finished, thQ process..." change to -- CAD is finished, the process --

UNITED STATES PATENT AND TRADEMARK OFFICE
CERTIFICATE OF CORRECTION

PATENT NO. : 7,106,835 B2
APPLICATION NO. : 10/124786
DATED : September 12, 2006
INVENTOR(S) : Richard Saalsaa It is certified that error appears in the above-identified patent and that said Letters Patent is hereby corrected as shown below:

Column 13, line 65, "...returns to pol5ng the communication file..." change to -- returns to polling the communication file --

Column 14, line 3, "...Moreover. sometimes pre-arrival..." change to -- Moreover, sometimes pre-arrival --

Column 14, line 8, "...of additional information that the..." change to -- of additional information the --

Column 14, line 12, "...and continue checking the communication..." change to -- and continues checking the communication --

Column 14, line 19, "...checking the communication rde for..." change to -- checking the communication file for --

Column 14, line 27, "...then a state fag=C test..." change to -- then a state flag=C test --

Column 14, line 30, "...and wait 718 for the next..." change to -- and waits 718 for the next --

Column 14, line 52, "...or (2) can be used that is more like..." change to -- or (2) it can be used that is more like --

Column 14, line 55, "...passed a "S" state flag..." change to -- passed an "S" state flag --

Column 15, line 13, "...control to saId computer aided..." change to -- control to said computer aided --

Column 15, line 31, "...process states fwlher comprises testing..." change to -- process states further comprises testing --

Column 16, line 14, "...value based one or more responses..." change to -- value based on one or more responses --

UNITED STATES PATENT AND TRADEMARK OFFICE
CERTIFICATE OF CORRECTION

| | |
|---|---|
| PATENT NO. | : 7,106,835 B2 |
| APPLICATION NO. | : 10/124786 |
| DATED | : September 12, 2006 |
| INVENTOR(S) | : Richard Saalsaa |

It is certified that error appears in the above-identified patent and that said Letters Patent is hereby corrected as shown below:

Column 16, line 38, "...capable of opelating both a computer..." change to -- capable of operating both a computer --

Signed and Sealed this

Seventh Day of August, 2007

JON W. DUDAS
*Director of the United States Patent and Trademark Office*